United States Patent [19]
Yamamoto et al.

[11] Patent Number: 5,242,411
[45] Date of Patent: Sep. 7, 1993

[54] PIERCING NEEDLE HAVING HYDROPHOBIC FILTER VENT

[75] Inventors: Masanobu Yamamoto; Kouhei Hayashi, both of Fujinomiya, Japan

[73] Assignee: Terumo Kabushiki Kaisha, Tokyo, Japan

[21] Appl. No.: 821,426

[22] Filed: Jan. 15, 1992

[30] Foreign Application Priority Data

Jan. 18, 1991 [JP] Japan .................. 3-1181[U]

[51] Int. Cl.[5] ............................................ A61M 5/178
[52] U.S. Cl. ................................... 604/167; 604/168
[58] Field of Search ............. 604/168, 126, 264, 164, 604/167, 93

[56] References Cited

U.S. PATENT DOCUMENTS

| | | |
|---|---|---|
| 3,312,220 | 4/1967 | Eisenberg . |
| 4,149,535 | 4/1979 | Volder ........................ 604/164 X |
| 4,200,096 | 4/1980 | Charvin ...................... 604/168 X |
| 4,416,290 | 11/1983 | Lutkowski . |
| 4,610,665 | 9/1986 | Matsumoto et al. . |
| 4,675,017 | 6/1987 | Sato ........................... 604/126 X |
| 4,682,980 | 7/1987 | Suzuki ........................ 604/168 X |
| 4,917,671 | 4/1990 | Chang ........................ 604/168 |
| 4,935,010 | 6/1990 | Cox et al. . |
| 5,032,116 | 7/1991 | Peterson et al. ............ 604/168 |
| 5,104,389 | 4/1992 | Deem et al. ................. 604/167 X |

FOREIGN PATENT DOCUMENTS

| | | |
|---|---|---|
| 0139091 | 5/1985 | European Pat. Off. . |
| 0223451 | 7/1987 | European Pat. Off. . |
| 0268480 | 5/1988 | European Pat. Off. . |
| 60-88562 | 5/1985 | Japan . |
| 63-197463 | 8/1988 | Japan . |

Primary Examiner—John J. Wilson
Assistant Examiner—Jeffrey A. Smith
Attorney, Agent, or Firm—Frishauf, Holtz, Goodman & Woodward

[57] ABSTRACT

A piercing needle with which a flashback can be reliably confirmed and air can be prevented from remaining in its hub portion. The piercing needle comprises an outer needle having a hub, an inner needle to be inserted into the outer needle, a hub portion of which is adapted to be fitted in the outer needle hub, and a valve disc to close the internal cavity of the outer needle. Side holes are formed in the distal end of the outer needle. The outer needle hub is provided with a hydrophobic vent filter near the valve disc to allow the internal cavity of the outer needle hub to communicate with the outer atmosphere.

9 Claims, 6 Drawing Sheets

PIERCING NEEDLE HAVING HYDROPHOBIC FILTER VENT

BACKGROUND OF THE INVENTION

1. Field of the Invention

The present invention relates to a piercing needle which is temporarily indwelled in a blood vessel in performing, e.g., blood transfusion or fluid therapy.

2. Description of the Related Art

Conventionally, when blood transfusion or fluid transfusion, for example, is to be performed into a blood vessel, a piercing needle is pierced into a blood vessel with its inner and outer needles assembled together. Thereafter, only the inner needle is pulled out, and a connector of, e.g., a blood transfusion set (or a fluid therapy set) is connected to an outer needle hub, thereby performing the operation of interest. However, during the manipulation of pulling out the inner needle and connecting the connector, blood may leak from the outer needle hub. In order to prevent this blood leakage, piercing needles in each of which a valve disc is provided in an outer needle hub have been conventionally proposed (Unexamined Published Japanese Patent Application Nos. 60-88562 and 63-197463).

In such a conventional puncturing needle incorporating a valve disc, however, when an inner needle is pulled out during a manipulation, air remaining in an outer needle hub cannot be vented due to the sealing properties of the valve disc itself. For this reason, the outer hub cannot be filled with blood, and this makes it impossible to confirm a so-called flashback in the outer needle hub unless a specially cumbersome manipulation is performed.

To solve the above problems, Unexamined Published Japanese Patent Application No. 63-197463 proposes an injection device in which vent means is provided in the side wall of coupling means corresponding to the outer needle hub to vent air from the coupling means chamber and to prevent leakage of a liquid.

The vent means disclosed in the above proposal, however, adopts a structure in which a cylindrical hole is formed in the side wall of the coupling means and a cylindrical filter is fitted in the hole. Therefore, the manufacture of the puncturing needle is complicated and results in a high cost, and there is another disadvantage that the filter may be removed during the manufacture. In addition, during the blood vessel piercing manipulation, the filter portion may be closed with fingers, thus disenabling the reliable confirmation of a flashback. Furthermore, the vent means disclosed in the above proposal has a saddle for preventing blood from being brought into contact with air through the filter. This saddle is formed outside the coupling means and can slide to cover the film. However, this saddle mechanism also has a complicated structure, and this also results in a cumbersome manufacture or a complicated manipulation. In other words, this saddle lacks reliability and ease in manipulation.

In addition, since the position of the filter is separated from the position of the valve, air in the hub may remain between the filter and the valve disc.

SUMMARY OF THE INVENTION

The present invention has been made as to solve the above problems and has as its object the provision of a piercing needle or cannula in which a flashback can be reliably confirmed with a simple structure in which no air remains in a hub, and blood is not brought into contact with air through a filter thereby increasing the safety of the piercing needle.

In order to achieve the above object, there is provided a piercing needle comprising a cylindrical outer cannular or needle, an outer needle hub fixed to a proximal end of the outer needle and having an internal cavity which communicates with the outer needle, an inner needle which is provided to be freely inserted in and removed from the outer needle through the outer needle hub and adapted to be inserted in the outer needle such that a needle tip of the inner needle projects from a distal end of the outer needle, an inner needle hub which is fixed to a proximal end of the inner needle and can be fitted in the outer needle hub, and a valve disc which is extended to close the internal cavity of the outer needle hub, and through which a rod-like member can be inserted, wherein side holes are formed in a distal end portion of the outer needle to communicate with a gap between the outer and inner needles and with the internal cavity of the outer needle hub, and the outer needle hub includes a vent filter which allows the internal cavity of the outer needle hub to communicate with the outer atmosphere, the vent filter being adjacent to the valve disc.

The valve disc has a disk-like portion, and cut portions are formed in this disk-like portion. Upon insertion of the rod-like member or the tubular member into this thin-wall portion, the central portion of the valve disc is turned up forward. This turned portion of the valve disc covers the inner circumferential surface of the vent filter.

The inner needle hub which is fitted in the outer needle hub is pierced in a blood vessel. In this case, since the present invention includes the vent filter provided adjacent to the valve disc in the outer needle hub, air originally present in the outer needle hub is pushed out from this filter portion by the blood pressure of blood flowing from the side hole formed in the outer needle. As a result, air which is present in a position close to the valve disc on the inner circumferential surface of the outer needle hub where air is most likely to remain can be removed and replaced with blood.

By connecting the connector as the rod-like member to the outer needle hub, the central portion of the valve disc having the cuts is turned up forward. The inner circumferential portion of the ring-like vent filter is covered with this turned portion of the valve disc.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

Figure 1:
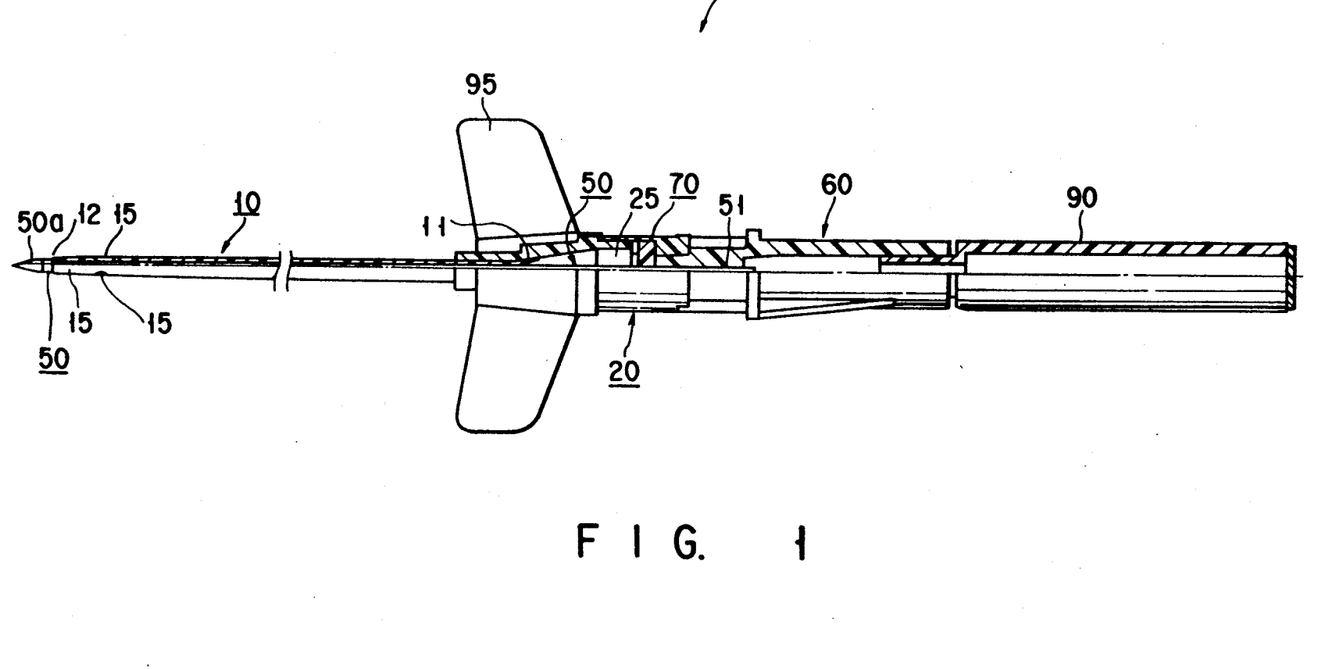
FIG. 1 is a partially sectional view showing a piercing needle according to the present invention.

An embodiment of a piercing needle according to the present invention will be described below with reference to FIGS. 1 to 10. FIG. 1 is a partially sectional view showing the piercing needle according to the present invention. As shown in FIG. 1, a piercing needle 1 of the present invention has a cylindrical outer needle (cannula) 10; an outer needle hub 20 fixed to a proximal end 11 of the outer needle 10 and having an internal cavity 25 which communicates with the outer needle 10; an inner needle 50 which is provided to be freely inserted in and removed from the outer needle 10 through the outer needle hub 20 and is fitted in the outer needle 10 so that its needle tip projects from a distal end 12 of the outer needle 10; an inner needle hub 60 which is fixed to a proximal end 51 of the inner needle 50 and can be fitted in the outer needle hub 20; and a valve disc 70 which is extended to close the internal cavity 25 of the outer needle hub 20 and through which a rod-like member or a tubular member (not shown) can be inserted. In addition, the outer needle hub 20 has air vent holes 27 (shown in FIG. 2) which allow the internal cavity 25 of the outer needle hub 20 to communicate with the outer atmosphere. A ring-like vent filter 80 is provided at the end portions of the air vent holes 27 on the internal cavity side.

More specifically, at least one side hole (in this embodiment, three side holes 15 are illustrated) is formed in the distal end portion of the outer cannula or needle 10. Therefore, even when the outer needle 10 and the inner needle 50 are assembled together, the outer atmosphere and the internal cavity 25 of the outer needle hub 20 communicate with each other through these side holes 15. That is, although the distal end 12 of the outer needle 10 is in tight contact with the inner needle 50, a small gap is formed between the outer needle 10 and the inner needle 50 except for that portion. As the outer needle 10, a plastic needle consisting of a fluorine-based resin such as Teflon or an olefine-based resin such as polypropylene or polyethylene is commonly used.

Figure 2:
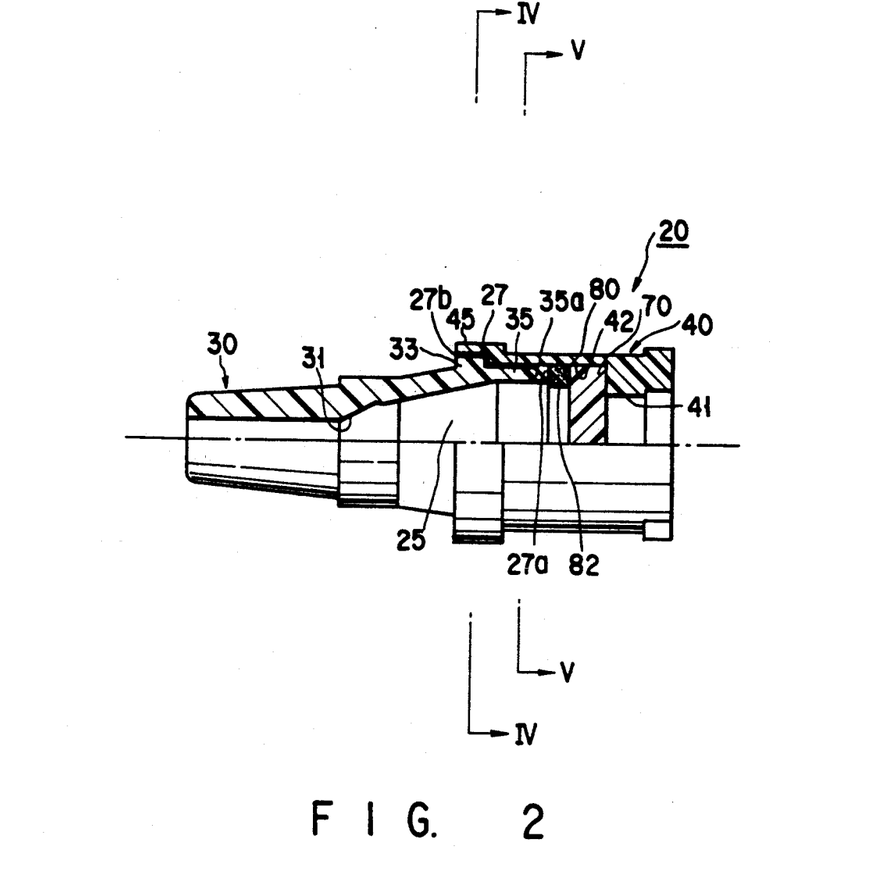
FIG. 2 is a partially sectional view showing an outer needle hub which is one component of the piercing needle according to the present invention; r
Figure 3:
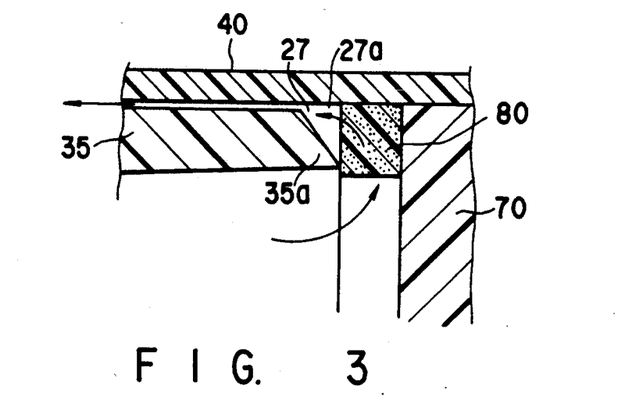
FIG. 3 is an enlarged view showing a portion around a vent filter shown in FIG. 2.
Figure 4:
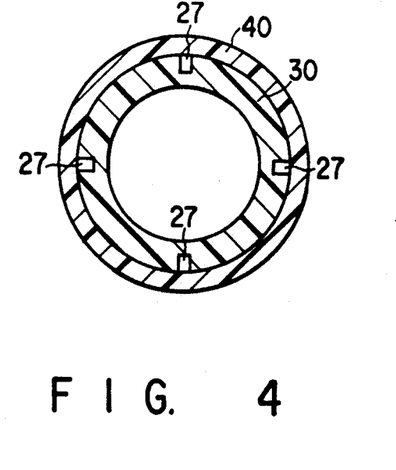
FIG. 4 is a sectional view taken along a line IV—IV of FIG. 2.
Figure 5:
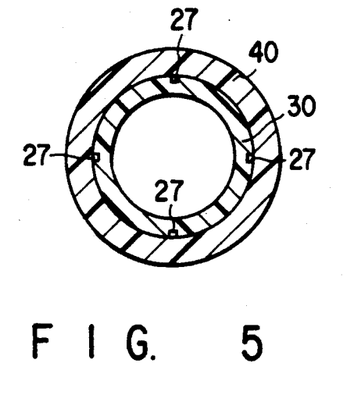
FIG. 5 is a sectional view taken along a line V—V of FIG. 2.

As shown in FIG. 2, the outer needle hub 20 fixed to the proximal end 11 of the outer needle 10 has the air vent holes 27 which allow the internal cavity 25 of the outer needle hub 20 to communicate with the outer atmosphere. In this embodiment, the outer needle hub 20 is constituted by two components, and this facilitates not only the formation of the air vent holes 27 but also the insertion of the vent filter 80 and the valve disc 70 into the outer needle hub 20 as will be described below. That is, the outer needle hub 20 is constituted by two parts, a first outer needle hub body 30 and a second outer needle hub body 40. The first outer needle hub body 30 is substantially cylindrical and has a tapered portion 31 for caulking and fixing the outer needle 10 in its internal cavity The first outer needle hub body 30 also has a projecting portion 33 and a flat portion 35 on the outer circumferential surface of its rear end portion. A rear end portion 35a of this flat portion 35 is tapered and in contact with the filter 80 to be described later (FIG. 3). In addition, as shown in FIGS. 4 and 5, continuous trenches for forming the air vent holes 27 are formed in the outer circumferential surfaces of the projecting portion 33 and the flat portion 35 of the first outer needle hub body 30. It is preferable to form a plurality of such trenches (air vent holes 27) particularly with equal intervals therebetween along the circumferential direction. The second outer needle hub body 40, on the other hand, is also cylindrical. A tapered surface 41, and more preferably a lure-tapered surface, in which a rod-like member such as a connector (to be described later) is fitted, is formed in the rear portion of an internal cavity of the second outer needle hub body 40. In addition, a recess portion 42 for inserting the valve disc 70 and the vent filter 80 to be described later is formed. The front portion 45 (shown in FIG. 2) of an internal cavity of the second outer needle hub body 40 is shaped such that the projecting portion 33 and the flat portion 35 of the first outer needle hub body 30 are fitted in that portion, and this fitting forms the air vent holes 27. As a result, the outer needle hub 20 has a projecting portion on its outer circumferential surface along the circumferential direction, and an outer atmosphere-side end portion 27b of each air vent hole is located on the side surface of this projecting portion. Therefore, even when the piercing needle is handled while the outer circumferential surface of the outer needle hub 20 is held during piercing, these holes are not closed with fingers. Note that in the formation of the air vent holes 27, the trenches need not be formed in the outer circumferential surface of the first outer needle hub body 30 but may be formed in the inner circumferential surface of the second outer needle hub body 40.

The ring-like vent filter 80 is provided at internal cavity-side end portions 27a of the air vent holes 27 in the internal cavity of the outer needle hub 20. This vent filter 80 has pores through which air can pass but a liquid such as blood cannot. The range of the average pore size of the filter 80 may be 0.01 to 0.5 $\mu$m, preferably 0.1 to 0.2 $\mu$m. The filter is constituted by, e.g., a hydrophobic nonwoven fabric consisting of polypropylene or polyethylene, a polypropylene porous film, a sintered hydrophobic filter consisting of a fluorine-based resin or a polyolefin-based resin such as polypropylene or polyethylene, or a swollen filter containing a starch-sodium acrylate graft polymer and polyethylene. The swollen filter is preferably air-permeable before the filter is swollen.

Figure 6:
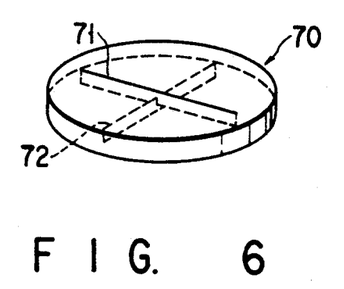
FIG. 6 is a perspective view showing an example of a valve disc.
Figure 7:
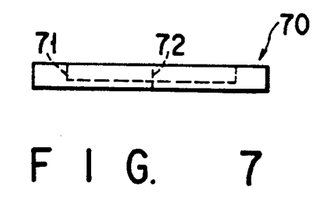
FIG. 7 is a side view of FIG. 6.

The valve disc 70 is provided behind and adjacent to the vent filter 80. The valve disc 70 especially preferably has a function of preventing a blood leakage from the outer needle hub 20 when the inner needle is pulled out and a connector or the like as the rod-like member is connected during the manipulation, and a function (FIG. 10) in which the central portion of the valve disc is turned up forward (toward the distal end) upon insertion of the rod-like member or the tubular member into the valve disc 70 and this turned portion of the valve disc covers an inner circumferential surface 82 (FIG. 2) of the ring-like vent filter 80. With these function (particularly the latter), in the situation in which the outer needle 10 is closed while a connector or the like is connected and blood is supplied by a blood pump through the outer needle, a flow of air from the vent filter 80 into the internal cavity 25 can be prevented even if a load is applied on the internal cavity 25, thereby preventing blood from being brought into contact with the outer air through the vent filter 80. A so-called Y-cut valve or cross-cut valve can be used as the valve disc 70 having the above functions. A most preferable practical example is one having a structure similar to that disclosed in Unexamined Published Japanese Patent Application No. 60-88562. That is, as shown in FIGS. 6 and 7, a disk-like portion of this valve, which consists of a flexible substance, such as silicone rubber, is linearly cut from both the upper and lower surfaces, thereby forming first and second cut portions 71 and 72 which cross each other at the substantially central portion.

The assembly of the inner needle hub 60 and the inner needle 50 can be inserted into the assembly of the outer needle hub 20 and the outer needle 10. Note that as shown in FIG. 1, a filter cap 90 having air permeability may be provided in the rear end portion of the inner needle hub 60, or a wing 95 for facilitating fixing may be formed on the lower surface of the outer needle hub 20.

A rotation-stop mechanism (not shown) for adjusting the needle tip of the inner needle 50 is normally provided near the fitted portion of the inner and outer needle hubs 60 and 20.

Note that the first and second outer needle hubs 30 and 40 constituting the outer needle hub 20 are commonly formed of a transparent or translucent plastic material so that a flashback can be visually confirmed.

The manipulation of the piercing needle described above will be described below.

Figure 8:
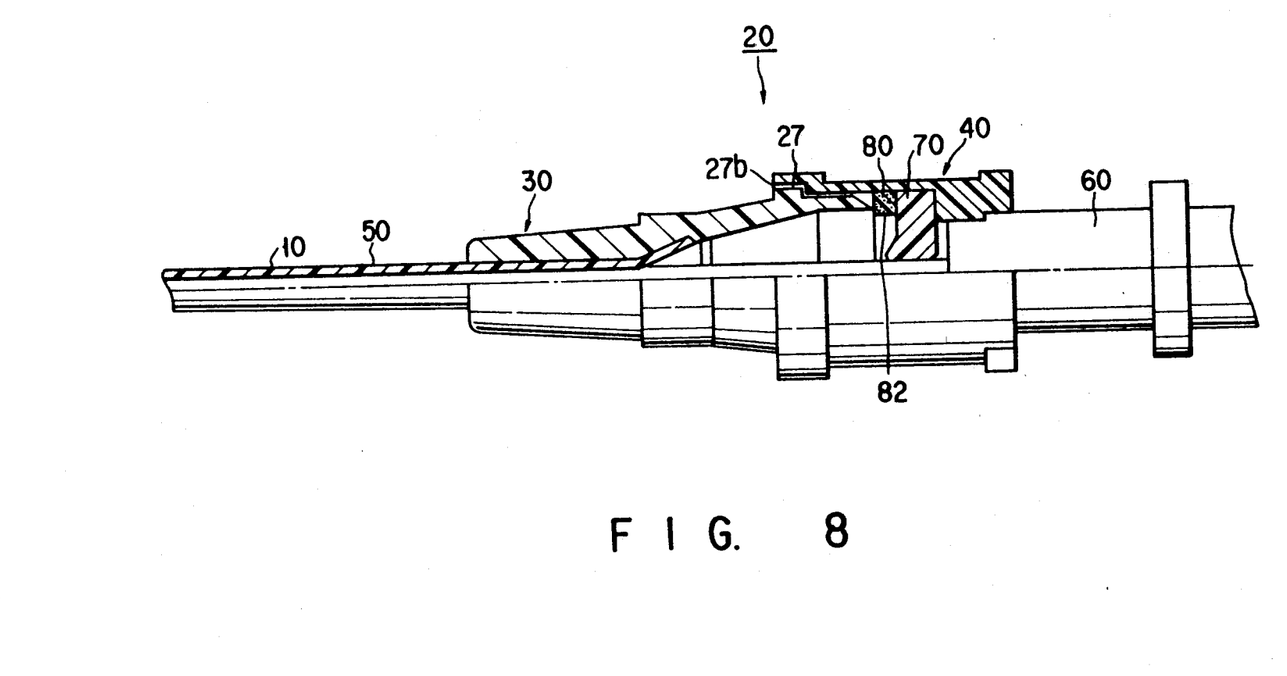
FIG. 8 is a partially sectional view for explaining the manipulation of the piercing needle according to the present invention.
Figure 9:
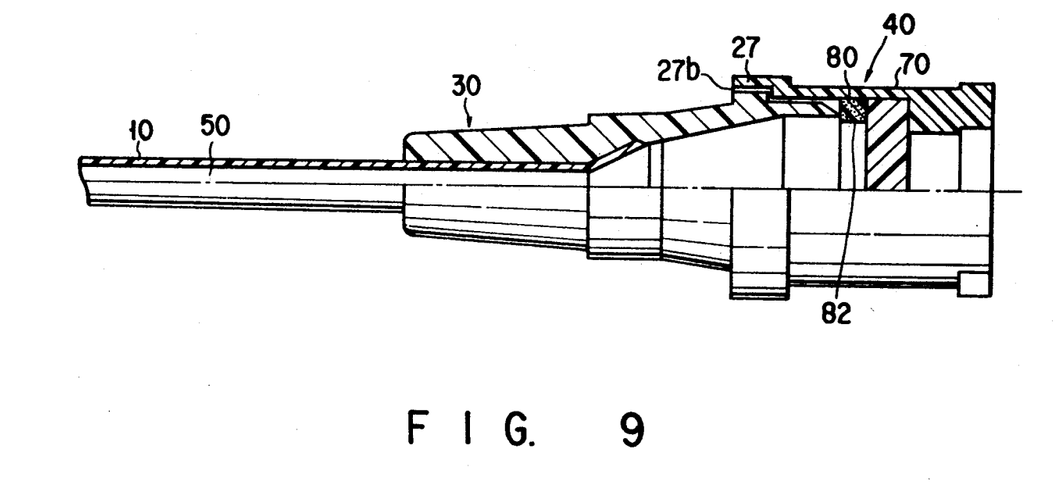
FIG. 9 is a partially sectional view for explaining the manipulation of the piercing needle according to the present invention.

First, as the state before the use, the inner needle 50 is inserted in the outer needle 10 through the outer needle hub 20, as shown in FIG. 1. When the inner needle hub 60 is completely inserted in the proximal end portion of the outer needle hub 20, a needle tip 50a of the inner needle 50 projects from the distal end of the outer needle 10, and this enables smooth piercing into a blood vessel or the like. At this time, the inner needle 50 and the valve disc 70 are in tight contact with each other, as shown in FIG. 8. The piercing needle in this state is pierced into, e.g., a blood vessel to introduce the outer needle 10 and the inner needle 50 together into the blood vessel. In this case, blood flows from the side holes 15 formed in the distal end portion of the outer needle 10 into the internal cavity 25 of the outer needle hub 20. As shown in FIG. 3, air in the outer needle hub 20 is pushed out from the vent filter 80 by a blood pressure and replaced with blood, and this makes it possible to confirm a flashback. Subsequently, the inner needle 50 is pulled out from the outer needle hub 20 (FIG. 9). In this case, the valve disc 70 naturally closes to prevent a blood leakage from the outer needle hub 20. Thereafter, as shown in FIG. 10, a connector 100 as the rod-like member or the tubular member of a blood transfusion or fluid transfusion set (not shown) is inserted in the outer needle hub 20 and fixed such that the distal end portion of the connector 100 extends through the valve disc 70.

Figure 10:
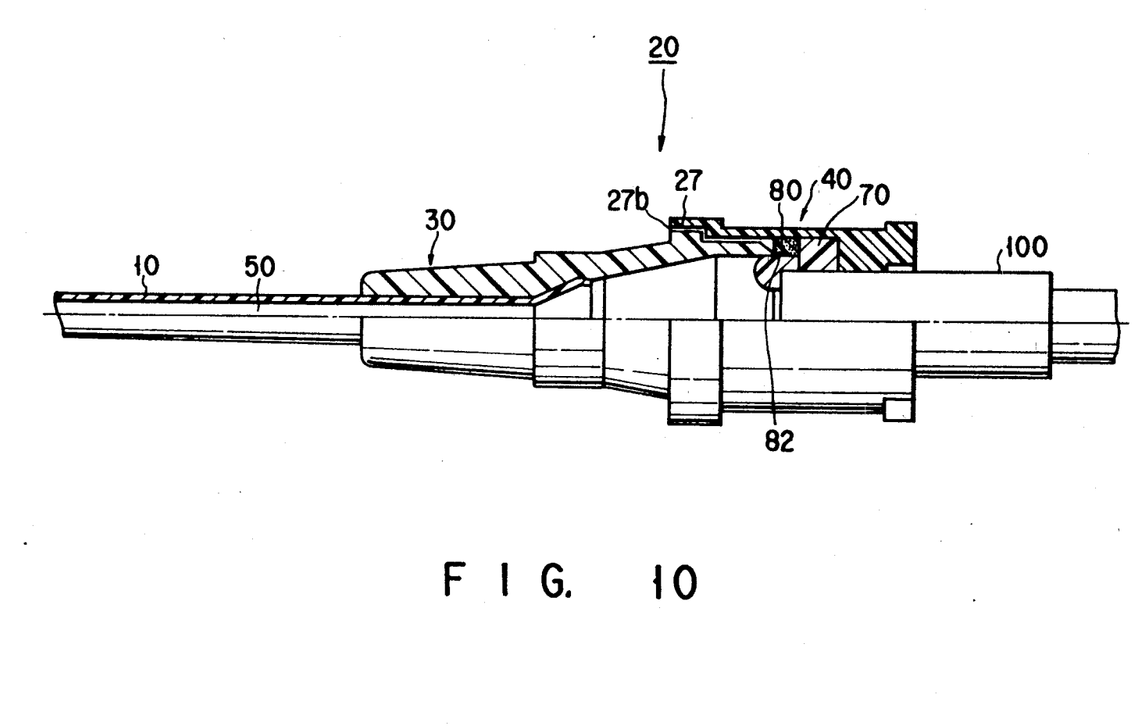
FIG. 10 is a partially sectional view for explaining the manipulation of the piercing needle according to the present invention.

At this time, the valve disc 70 deforms, and this deformation turns up the central portion of the valve disc forward, as shown in FIG. 10. This turned portion of the valve disc consequently covers the inner circumferential surface 82 of the ring-like vent filter.

The outer needle hub of the piercing needle according to the present invention has air vent holes which allow the internal cavity of the outer needle hub to communicate with the outer atmosphere, and the vent filter provided at the internal cavity-side end portions of the air vent holes. Therefore, when the inner needle hub fitted in the outer needle hub is pierced into a blood vessel, air in the outer needle hub is pushed out from this filter portion by a blood pressure and replaced with blood. The result is easy and reliable confirmation of a flashback. The manufacture of this piercing needle is also easy. In addition, since the vent filter is provided adjacent to the valve disc extended in the outer needle hub, it is possible to effectively remove air in a portion close to the valve disc on the inner circumferential surface of the outer needle hub. Furthermore, the outer needle hub has a projecting portion on its outer circumferential surface along the circumferential direction, and the outer atmosphere-side end portions of the air vent holes are formed in the side surface of this projecting portion. Therefore, even when the blood vessel piercing is performed by holding the outer circumferential surface of the outer needle hub, the air vent holes are prevented from being closed with fingers. When a connector as the rod-like member or the tubular member is connected to the outer needle hub, the central portion of the valve disc having the cuts is turned up forward, and the inner circumferential surface of the ring-like vent filter is covered with this turned portion of the valve disc. As a result, blood is prevented from being brought into contact with the outer air through the vent filter.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A piercing needle comprising:
   a cylindrical outer needle;
   an outer needle hub fixed to a proximal end of said outer needle, said outer needle hub having an internal cavity which communicates with said outer needle;
   an inner needle, freely insertable into and removable from said outer needle through said outer needle hub, said inner needle being insertable into said outer needle such that a needle tip of said inner needle projects from a distal end of said outer needle;
   an inner needle hub fixed to a proximal end of said inner needle, said inner needle hub fitting into said outer needle hub; and
   a valve disc that is extended to close said internal cavity of said outer needle hub;
   a rod member insertable through said valve disc; and
   wherein:

a plurality of side holes are formed in a distal end portion of said outer needle to allow said internal cavity of said outer needle hub to be in fluid communication with an outer atmospheric pressure through said side holes even when said outer and inner needles are assembled together;

said outer needle hub includes a plurality of air vent holes which allow said internal cavity of said outer needle to be in fluid communication with said outer atmospheric pressure, and a vent hydrophobic filter interposed between a plurality of internal cavity-side end portions of said air vent holes and said valve disc; and said valve disc includes a disk portion having cut portions therein, such that when said rod member is inserted in said valve disc through said cut portions, a central portion of said valve disc is moved away from a center axis of said valve disc in a forward insertion direction of said rod so that the moved away central portion of said valve disc covers an inner circumferential surface of said vent filter.

2. A needle according to claim 1, wherein said vent filter is ring shaped.

3. A piercing needle comprising:

a cylindrical outer needle;

an outer needle hub fixed to a proximal end of said outer needle, said outer needle hub having an internal cavity that is in fluid communication with said outer needle;

an inner needle, freely insertable into and removable from said outer needle through said outer needle hub, said inner needle being insertable into said outer needle such that a needle tip of said inner needle projects from a distal end of said outer needle;

an inner needle hub fixed to a proximal end of said inner needle, said inner needle hub fitting into said outer needle hub;

a valve member that is extended to close said internal cavity of said outer needle hub;

a rod member insertable through said valve member;

a vent filter positioned at an inner surface of, and adjacent to, said valve member to allow said internal cavity of said outer needle hub to be in fluid communication with an outer atmospheric pressure; and said outer needle hub includes a projected portion on an outer circumferential surface thereof, said projected portion having a plurality of air vent holes formed in side surfaces thereof for providing a fluid communication path to said internal cavity of said outer needle hub via said vent filter.

4. A piercing needle according to claim 3, wherein said vent filter is ring shaped.

5. A piercing needle comprising:

a cylindrical outer needle;

an outer needle hub fixed to a proximal end of said outer needle, said outer needle hub having an internal cavity that is in fluid communication with said outer needle;

an inner needle, freely insertable into and removable from said outer needle through said outer needle hub, said inner needle being insertable into said outer needle such that a needle tip of said inner needle projects from a distal end of said outer needle;

an inner needle hub fixed to a proximal end of said inner needle, said inner needle hub fitting into said outer needle hub;

a valve member that is extended to close said internal cavity of said outer needle hub;

a rod member insertable through said valve member;

a hydrophobic vent filter provided at an inner surface of, and adjacent to, said valve member to provide said internal cavity of said outer needle hub with a fluid communication path to an outer atmospheric pressure; and a projected portion formed on an outer circumferential surface of said outer needle hub, said projected portion having a plurality of air vent holes formed in a side surface thereof for providing a fluid communication path to said internal cavity of said outer needle hub via said vent filter.

6. A needle according to claim 5, wherein said vent filter is ring shaped.

7. A piercing needle comprising:

a cylindrical outer needle;

an outer needle hub fixed to a proximal end of said outer needle, said outer needle hub having an internal cavity that is in fluid communication with said outer needle;

an inner needle, freely insertable into and removable from said outer needle through said outer needle hub, said inner needle being insertable into said outer needle such that a needle tip of said inner needle projects from a distal end of said outer needle;

an inner needle hub fixed to a proximal end of said inner needle, said inner needle hub fitting into said outer needle hub;

a valve member that is extended to close said internal cavity of said outer needle hub;

a rod member insertable through said valve member;

a plurality of air vent holes formed in said outer needle hub, said plurality of air vent holes allowing said internal cavity of said outer needle hub to be in fluid communication with an outer atmospheric pressure;

a vent filter interposed between a plurality of internal cavity-side end portions of said plurality of air vent holes and said valve member; and a disk portion of said valve member having cut portions; wherein when: said rod member is inserted in said valve member through said cut portions of said disc portion, a central portion of said valve member is moved away from a center axis of said valve member in a forward insertion direction of said rod member away from said rod member so that the moved away portion of said valve member covers an inner circumferential surface of said vent filter.

8. A needle according to claim 7, wherein said vent filter is ring shaped.

9. A needle according to claim 7, wherein said vent filter is hydrophobic.

* * * * *